United States Patent
Basilion (10) Patent No.: US 9,192,302 B2
(45) Date of Patent: *Nov. 24, 2015

(54) INTRA-OPERATIVE MOLECULAR IMAGING

(75) Inventor: James Basilion, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/288,611

(22) Filed: Nov. 3, 2011

(65) Prior Publication Data

US 2012/0116230 A1    May 10, 2012

Related U.S. Application Data

(63) Continuation of application No. 11/811,818, filed on Jun. 12, 2007, now Pat. No. 8,078,264.

(60) Provisional application No. 60/819,865, filed on Jul. 11, 2006.

(51) Int. Cl.
*A61B 5/00* (2006.01)
*A61B 19/00* (2006.01)
*A61K 49/00* (2006.01)

(52) U.S. Cl.
CPC ............ *A61B 5/0059* (2013.01); *A61B 5/0071* (2013.01); *A61B 2019/5231* (2013.01); *A61K 49/0017* (2013.01)

(58) Field of Classification Search
CPC .............. A61B 5/0059; A61B 5/0071; A61B 2019/5231; A61K 49/0017

USPC ................................................. 600/473, 476
See application file for complete search history.

(56) References Cited

U.S. PATENT DOCUMENTS

| | | | |
|---|---|---|---|
| 5,515,864 A * | 5/1996 | Zuckerman | 600/311 |
| 6,083,486 A | 7/2000 | Weissleder et al. | |
| 6,152,870 A * | 11/2000 | Diener | 600/107 |
| 6,395,518 B1 | 5/2002 | Mayrand | |
| 6,403,812 B1 | 6/2002 | Menchen et al. | |
| 6,632,401 B1 | 10/2003 | Wulf | |
| 7,977,058 B2 | 7/2011 | Low | |

(Continued)

FOREIGN PATENT DOCUMENTS

WO     20100138738 A1     12/2010

OTHER PUBLICATIONS

Veiseh et al., Turn or Paint: Chlorotoxin: Cy5.5 Bioconjugate. . . . , Cancer Res. 2007; 67(14). Jul. 15, 2007, pp. 6882-6888, (I2007 Amer. Assoc. for Cancer Research.

(Continued)

*Primary Examiner* — Jonathan Cwern
(74) *Attorney, Agent, or Firm* — Tarolli, Sundheim, Covell & Tummino LLP (57) ABSTRACT

A system for imaging an abnormal cell and or diseased tissue after topical application of a near infrared protease-specific probe is disclosed. The system includes a protease-specific near infrared (NIRF) imaging probe, means for topically administering the protease-specific probe to a diseased tissue and an imaging device capable of detecting the interaction between the protease-specific NIRF imaging probe and the diseased tissue. A method and surgical procedure are also disclosed.

16 Claims, 10 Drawing Sheets

(56) References Cited

U.S. PATENT DOCUMENTS

2004/0087862 A1* 5/2004 Geng .................... 600/473
2007/0036725 A1 2/2007 Bogyo et al.

OTHER PUBLICATIONS

Weissleder et al., "In Vivo Imaging of Tumors with Protease-activated near-infrared Fluorescent Probes", Nature Biotechnology, vol. 17, Apr. 1999.

Urano, Yasuteru, et al., "Rapid Cancer Detection by Topically Spraying a y-Glutamyltranspeptidase—Activated Fluorescent Probe", Sci Tmasl Med vol. 3, Issue 110, 110ra119 Nov. 23, 2011, pp. 1-10.

Martin Funovics, et al. "Protease sensors for bioimaging", Anal Bioanal Chem (2003) 377: 956-963.

Gang Zheng, et al. "Photodynamic molecular beacon as an activateable photosensitizer based on protease-controlled singlet oxygen quenching and activation", PNAS, May 22, 2007, vol. 104, No. 21: 8989-8994.

Galia Blum, et al. "Dynamic imaging of protease activity with fluorescently quenched activity-based probes", Nature Chemical Biology, vol. 1, No. 4, Sep. 2005.

Ralph Weissleder, et al. "In vivo imaging of tumors with protease-activated near-infrared fluorescent probes", Nature Biotechnology, vol. 17, Apr. 1999.

Omid Veiseh, et al. "Optical and MRI Multifunctional Nanoprobe for Targeting Gliomas", Nano Letters, 2005, vol. 5, No. 6: 1003-1008.

Ching-Hsuan Tung "Fluorescent Peptide Probes for In Vivo Diagnostic Imaging", Biopolymers (Peptide Science), vol. 76, 391-403 (2004).

Khalid Shah and Ralph Weissleder "Molecular Optical Imaging: Applications Leading to the Development of Present Day Therapeutics", NeuroRx: The Journal of the American Society for Experimental NeuroTherapeutics, vol. 2, 215-225, Apr. 2005.

Kelly B. Sexton, et al. Design of cell-permeable, fluorescent activity-based probes for the lysosomal cysteine protease asparaginyl endopeptidase (AEP)/legumain, Bioorganic & Medicinal Chemistry Letters 17 (2007): 649-653.

Marko Fonovic, et al. "Proteomics Evaluation of Chemically Cleavable Activity-based Probes", Molecular & Cellular Proteomics 6.10.

Umar Mahmood and Ralph Weissleder "Near-Infrared Optical Imaging of Proteases in Cancer", Molecular Cancer Therapeutics, vol. 2, 489-496, May 2003.

Yasuteru Urano, et al. "Rapid Cancer Detection by Topically Spraying a Rapid Cancer Detection by Topically Spraying a y-Glutamyltranspeptidase—Activated Fluorescent Probe", Science Translational Medicine, Nov. 23, 2011, vol. 3, issue 110, 110ra119.

* cited by examiner

Figure 10 ically required. This is largely due to a lack of precision and resolution of current intra-operative imaging techniques applied for these interventions.
INTRA-OPERATIVE MOLECULAR IMAGING

RELATED APPLICATION

This application is a continuation of U.S. patent application Ser. No. 11/811,818, filed Jun. 12, 2007 now U.S. Pat. No. 8,078,264 which claims priority from U.S. Provisional Application Ser. No. 60/819,865, filed Jul. 11, 2006, the subject matter of which are incorporated herein by reference in their entirety.

COPYRIGHT NOTICE

A portion of the disclosure of this patent document contains material subject to copyright protection. The copyright owner has no objection to the facsimile reproduction of the patent document or the patent disclosure as it appears in the Patent and Trademark Office patent file or records, but otherwise reserves all copyright rights whatsoever.

BACKGROUND

Conventional intra-operative imaging (IOI) may improve surgical results. However, conventional IOI may be limited by lack of resolution (e.g., approximately 0.9 mm). IOI may include, for example, MR (magnetic resonance) guided imaging. Conventional IOI may suffer from cramped surgical fields, surgery induced changes in MR enhancing tissues, difficulty in differentiating scar tissue from diseased tissue in patients that have previously undergone surgery, and so on. Thus, even "complete resections" guided by conventional IOI may not remove all abnormal cells associated with diseased tissue. For example, malignant cells that have infiltrated or are beginning to infiltrate at a tumor brain margin may not be removed.

Intra-operative MRI (magnetic resonance imaging) was introduced in 1997 for brain tumor surgery. Intra-operative MRI has been demonstrated to facilitate decreasing tumor burden over non-IOI augmented microscopic surgery. Intra-operative MRI may include, for example, gross initial excision followed by finer image-guided excision. Intra-operative MRI guided techniques may also include excision followed by image-guided radiological therapy. Conventional surgical excision aided by conventional IOI, limited as it is, has facilitated prolonging survival and quality of life.

Malignant gliomas affect approximately 15,000 people per year in the United States and remain difficult to treat. These gliomas present as focal masses within the brain substance and exhibit infiltrating margins in normal brain. Malignant gliomas produce a steady decline in quality of life and produce cumulative neurological and medical morbidities. Conventional therapeutic treatments (e.g., surgical excision, radiation) for malignant brain tumors (e.g., glioblastoma multiform) are at best palliative. These therapeutic treatments may include intra-operative navigational techniques and electrocorticographic mapping of involved motor and language areas. Other malignancies, brain diseases and abnormalities also remain difficult to treat. For example, treatment of epilepsy involves surgical resection of epileptic foci responsible for generating seizure activity in patients. The same technical challenges, to identify and mark abnormal cells or diseased tissues, posed for surgical resection of malignant gliomas exist for surgical resection of epileptic foci. Various imaging techniques and surgical techniques continue to evolve to meet these challenges.

Outside the brain, intra-operative navigational techniques and electrographic mapping are employed in the treatment of heart arrhythmias. Arrhythmias can occur in a healthy heart and be of minimal consequence. They also may indicate a serious problem and lead to heart disease, stroke or sudden cardiac death. Heat mediated and cryo-ablation are two conventional therapeutic treatments for heart arrhythmias. But like surgical techniques employed in the brain, the treatment can be harmful and affect a larger area of tissue than is therapeutically required. This is largely due to a lack of precision and resolution of current intra-operative imaging techniques applied for these interventions.

In some conventional examples, to attempt to identify abnormal cells, microscopic IOI techniques are combined with intravenously provided fluorescents dyes or drugs that home to diseased tissue and that may provide signals that are useful for imaging. These agents tend to fluoresce in the visible range. Unfortunately, significant background autofluorescence from the patient may make unambiguous detection of labeled diseased tissue problematic. These agents typically require systemic administration at doses that may approach those of therapeutics. Thus, translating these agents from clinical trial may be expensive and labor intensive, if possible at all. These agents also tend not to be associated with disease-specific molecular targets per se and thus do not provide the ability to exploit differential expression of molecular targets for added information during resection. Other techniques employing NIRF probes and systemic administration may require unacceptable intravenous dose requirements, unacceptable time to "develop" signal, and may depend on the vasculature for delivery, which may not provide probes to the region of interest.

BRIEF DESCRIPTION OF THE DRAWINGS

The accompanying drawings, which are incorporated in and constitute a part of the specification, illustrate various example systems, methods, and other embodiments of various aspects of the invention. It will be appreciated that the illustrated element boundaries (e.g., boxes, groups of boxes, or other shapes) in the figures represent one example of the boundaries. One of ordinary skill in the art will appreciate that in some embodiments one element may be designed as multiple elements, multiple elements may be designed as one element, an element shown as an internal component of another element may be implemented as an external component and vice versa, and so on. Furthermore, elements may not be drawn to scale.

DETAILED DESCRIPTION

Example systems and methods described herein concern identifying abnormal cells and/or diseased tissue without using intravenously provided imaging agents. To identify and thus to facilitate removing these abnormal cells, microscopic Intra-Operative Imaging (IOI) techniques are combined with topically applied molecular imaging markers for abnormal cells and/or diseased tissue. One with ordinary skill in the art will appreciate that identifying abnormal cells and diseased tissue may include labeling abnormal cells and/or labeling secreted molecular markers no longer associated with the abnormal cell. The example IOI techniques employ lower dose levels of optical imaging probes than conventional "near-therapeutic levels" techniques. Example techniques may involve topically administering either sub-pharmacologic doses of an agent or doses expected to produce a pharmacologic effect but not a toxic or other biological effect. Thus, the imaging agent is not delivered via intravenous injection, but rather via topical application, which facilitates localized probe diffusion. Specifically, the probe is topically delivered to the targeted tissue in a hydrophobic/hydrophilic solution that facilitates localized probe diffusion. An example hydrophobic/hydrophilic solution may include Dimethyl Sulfoxide (DMSO). The imaging agent may, for example, be detectable in the infrared (IR) spectrum.

In one example, a targeted fluorescent imaging probe can be topically applied as needed during surgery to interactively guide a surgeon and/or surgical instrument to remaining abnormal cells. The probe may be applied locally in low concentration, making it unlikely that pharmacologically relevant concentrations are reached. In one example, excess material may be removed (e.g., washed off) after a period of time (e.g., incubation period). In one example, the probe may target matrix metallproteases (MMPs) that are secreted from brain cells. Another example probe may be directed towards other families of proteases (e.g., cysteine proteases). Yet another example probe may be directed toward non-protease disease markers or abnormal cell markers. Probes may be detectable in a range of wavelengths (e.g., 400-900 nm).

Applications may include the use of a NIRF (near infrared) imaging scanner for IOI. The NIRF imaging scanner may facilitate detecting cells with which the topically applied imaging agent has interacted to produce a visually differentiated field. Another example may include a NIRF imaging scanner that facilitates detection of a cellular product secreted from the abnormal cell with which the topically applied imaging agent has interacted to produce a visually differentiated field. In one example, the NIRF scanner may be handheld. In another example, the NIRF scanner may be miniaturized and embedded in an apparatus (e.g., micro-machines, scalpel, neurosurgical cell removal device). Applications may also include acquiring images (e.g., MR, CT, optical) to guide and/or control subsequent activities including, but not limited to, developing a radiologic therapy plan, guiding a surgeon or surgical device (e.g., ablative laser), and so on.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Abnormal cell", as used herein refers to a cell that exhibits an elevated level of a protease or other molecular marker relative to normal cells in the same region of interest. An abnormal cell may exhibit an altered physiological activity relative to normal cells in the same region of interest. An abnormal cell may be, for example, a brain tumor cell that expresses an elevated level of Cathepsin L mRNA or an elevated level of Cathepsin L protein when compared to a non-tumor cell located in the same brain region. An abnormal cell may also be, for example, an epileptic cell that exhibits enhanced expression of Cathepsin L compared to a non-epileptic cell. In different examples, an abnormal cell may reside outside the brain and may exhibit an elevated level of protease or other molecular marker compared to a normal cell.

"Computer component", as used herein, refers to a computer-related entity (e.g., hardware, firmware, software, software in execution, combinations thereof). Computer components may include, for example, a process running on a processor, a processor, an object, an executable, a thread of execution, a program, and a computer. A computer component(s) may reside within a process and/or thread. A computer component may be localized on one computer and/or may be distributed between multiple computers.

"Computer communication", as used herein, refers to a communication between computing devices (e.g., computer, personal digital assistant, cellular telephone) and can be, for example, a network transfer, a file transfer, an applet transfer, an email, a hypertext transfer protocol (HTTP) transfer, and so on. A computer communication can occur across, for example, a wireless system (e.g., IEEE 802.11), an Ethernet system (e.g., IEEE 802.3), a token ring system (e.g., IEEE 802.5), a local area network (LAN), a wide area network (WAN), a point-to-point system, a circuit switching system, a packet switching system, and so on.

"Diseased tissue", as used herein refers to tissue that has an altered biological process or processes with corresponding alteration of cell function or structure and/or changes in gene expression and protein products relative to normal tissues in the same region of interest. Diseased tissue may include for example, an infiltrating glioma cell located at the margin of a brain tumor. Diseased tissue may also include epileptic tissue that exhibits abnormal electrical activity implicated in altering brain function. Diseased tissue may also include heart tissue that displays inappropriate electrical activity implicated in heart arrhythmias. Diseased tissue may also include, for example, Basal Cell Carcinoma, Squamous Cell Carcinoma of the skin, degenerating retina, Barretts esophagus, esophageal displasia, esophageal cancer, breast cancer, and so on.

"Logic", as used herein, includes but is not limited to hardware, firmware, software and/or combinations thereof to perform a function(s) or an action(s), and/or to cause a function or action from another logic, method, and/or system. Logic may include a software controlled microprocessor, discrete logic (e.g., application specific integrated circuit (ASIC)), an analog circuit, a digital circuit, a programmed logic device, a memory device containing instructions, and so on. Logic may include a gate(s), a combinations of gates, other circuit components, and so on. Where multiple logical logics are described, it may be possible in some examples to incorporate the multiple logical logics into one physical logic. Similarly, where a single logical logic is described, it may be possible in some examples to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"Signal", as used herein, includes but is not limited to, electrical signals, optical signals, analog signals, digital signals, data, computer instructions, processor instructions, messages, a bit, a bit stream, or other means that can be received, transmitted and/or detected.

"User", as used herein, includes but is not limited to, one or more persons, software, computers or other devices, or combinations of these.

Figure 1:
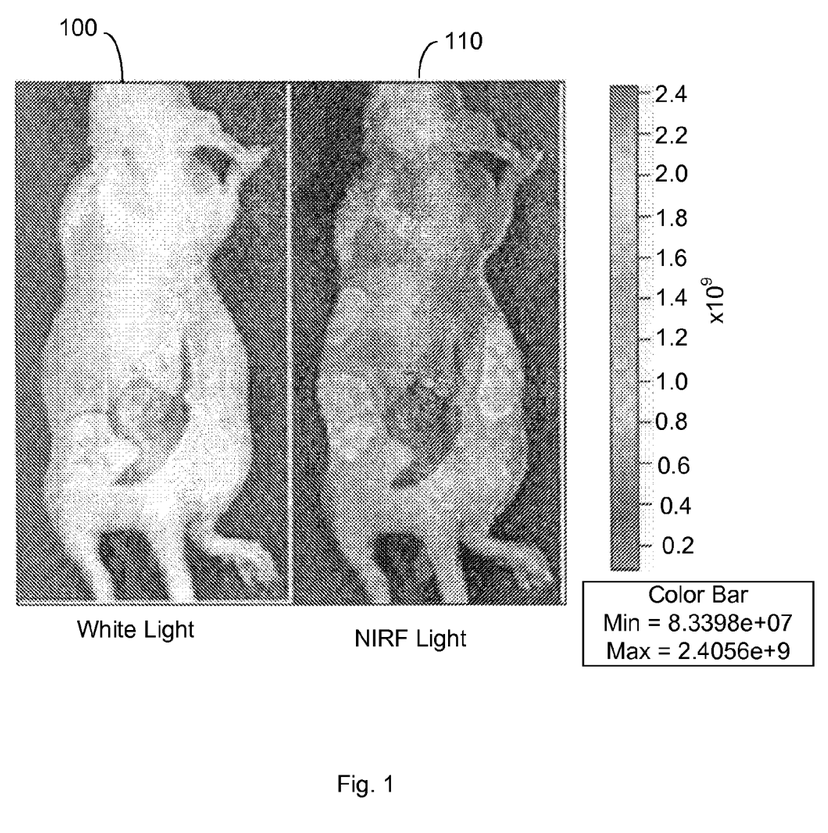
FIG. 1 illustrates an animal imaged before administration of a NIRF probe.

FIG. 1 illustrates an animal imaged before administration of a NIRF probe. Thus, FIG. 1 presents control images of animals with exposed tumors prior to application of a NIRF probe. Animal 100 illustrates an animal imaged in white light. Animal 110 illustrates an animal imaged in NIRF light.

Topical application of NIRF imaging probes facilitates identifying abnormal cell markers and facilitates the removal of abnormal cells during surgery. For example, topical application of NIRF imaging probes (e.g., protease specific probes) will image tumor associated markers (e.g., proteases) and delineate tumor margins accurately during resection. These images may facilitate, for example, guiding a surgeon and/or a surgical device (e.g., ablative laser) to non-excised diseased tissue. In another example, topical application of a NIRF imaging probe will image epileptic associated markers (e.g., proteases). The differentiation of epileptic tissue from non-epileptic tissue may allow for more precise resection of abnormal and/or diseased tissue during surgery. In another example, topical application of a NIRF imaging probe will image markers associated with cells displaying inappropriate electrical activity in the heart. Imaging of cells displaying inappropriate electrical activity may allow for more precise mapping of a cardiac foci and subsequent removal of this foci. Results of one such topical application are presented in FIG. 2.

Figure 2:
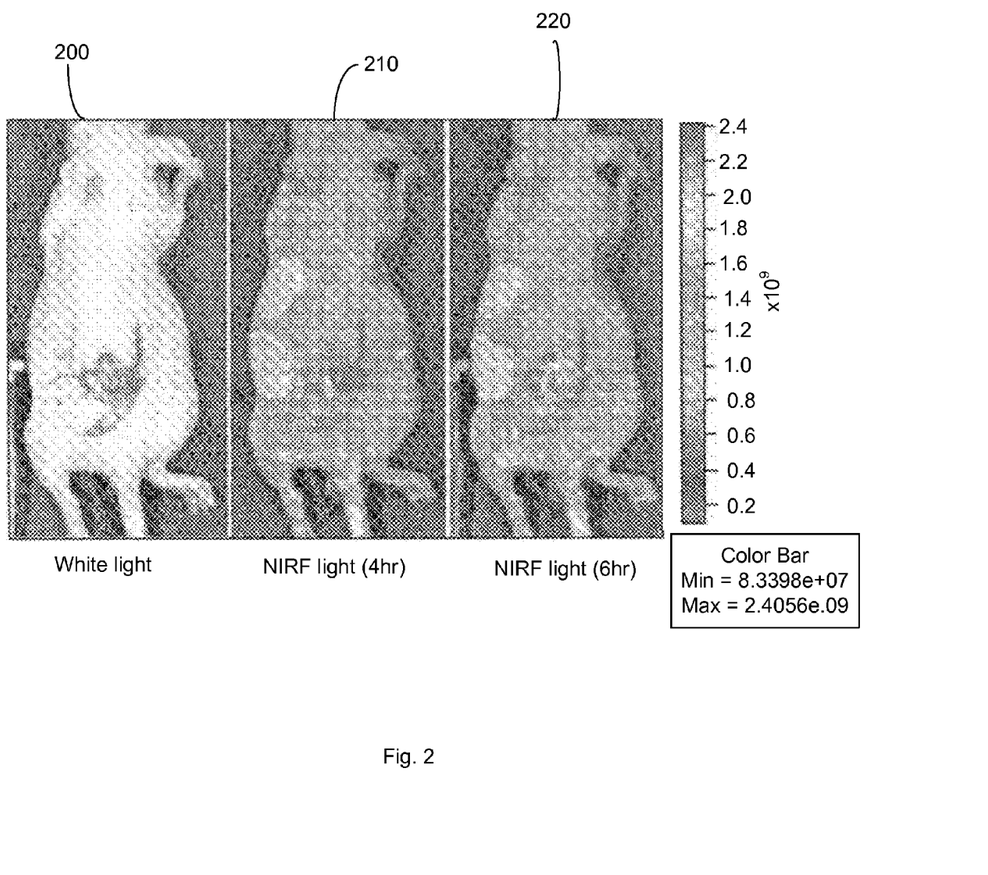
FIG. 2 illustrates an animal imaged after topical application of an activateable NIRF probe that is specific for MMP 2, 7, and 9.

FIG. 2 illustrates in vivo imaging of an animal after topical application of a NIRF probe. The tumor implanted in the animal illustrated in FIG. 2 overexpresses MMPs. While MMPs are described, it is to be appreciated that other proteases (e.g., cysteine proteases, serine proteases) may also be detected. While two proteases are described, it is to be appreciated that proteases from other families may be employed. Animal 200 is illustrated in a white light image. After four hours initial probe activation is visible as illustrated by animal 210. By six hours activation of the probe covers substantially all the tumor surface as illustrated by animal 220. While four and six hours are described, it is to be appreciated that NIRF probes having different reaction times (e.g., 5 minutes) may be employed.

Figure 3:
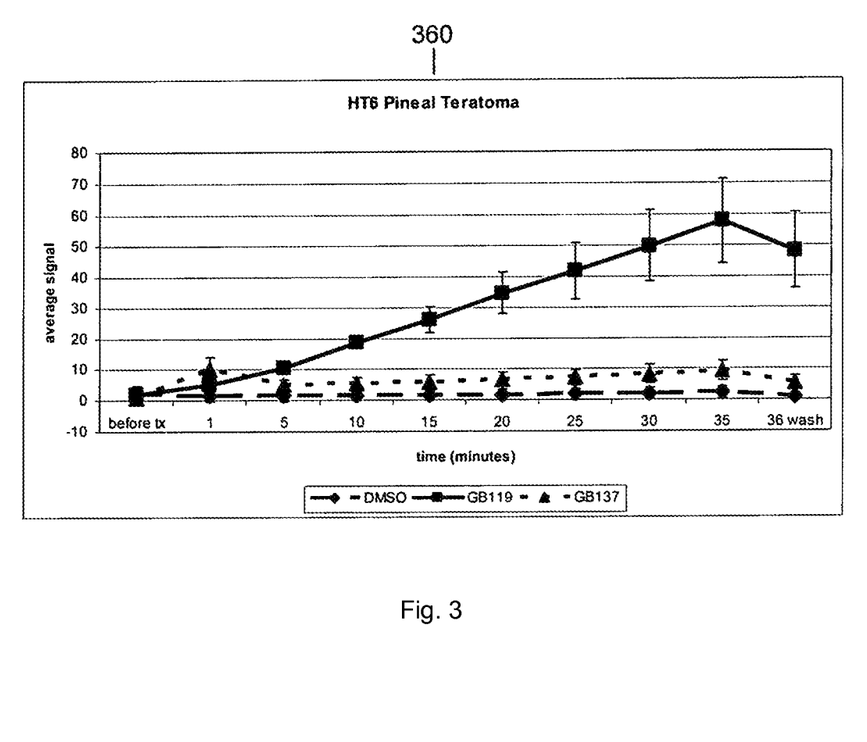
FIG. 3 illustrates imaged abnormal cells and/or cellular products of an abnormal cell in pineal teratoma tissue after topical application of either a NIRF probe specific for Cathepsin L (GB119) or a NIRF probe specific for Cathepsin B and L (GB137).

FIG. 3 illustrates activation of protease-specific NIRF probes following topical application to freshly isolated pineal teratoma tissue. GB119 is a probe that is activated by Cathepsin L. GB137 is a probe that is activated by Cathepsin B and Cathepsin L. The graph shows the average signal of each protease-specific NIRF probe prior to topical probe application to pineal teratoma tissue and at various time points following topical probe application to the tissue. The data presented in figure three illustrates a high level of probe activation following topical application of the protease-specific NIRF probe to pineal teratoma tissue.

Figure 4:
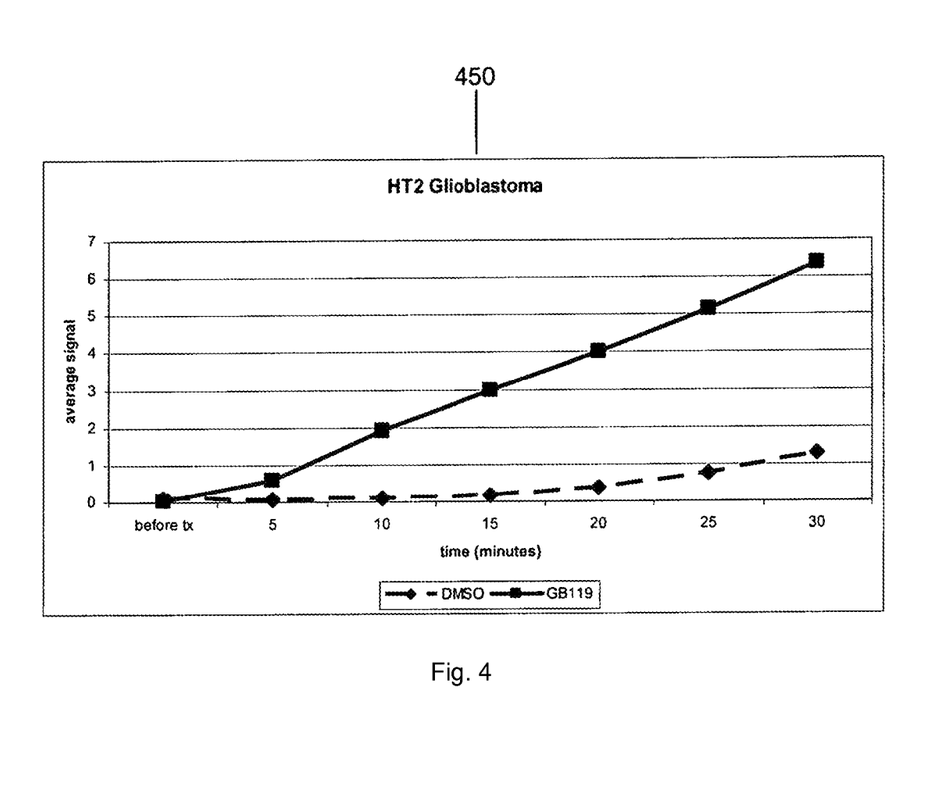
FIG. 4 illustrates imaged abnormal cells and/or cellular products of an abnormal cell in high-grade glioblastoma tissue after topical application of a NIRF probe specific for Cathepsin L.

FIG. 4 illustrates imaged abnormal cells and/or secreted cellular products of an abnormal cell in high-grade glioblastoma tissue following topical application of either a protease-specific NIRF probe or DMSO (control). The activation levels were translated into average signal and displayed in graphical form in graph 450.

Figure 5:
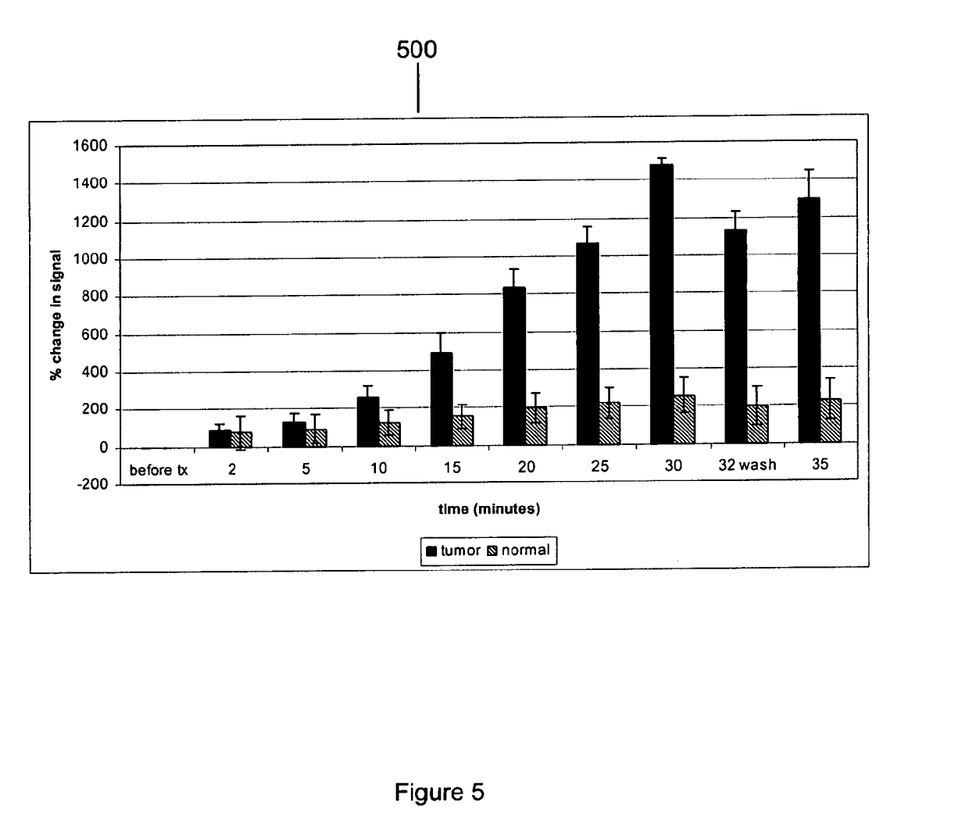
FIG. 5 illustrates a graphical representation of NIRF probe activation in adult human glioblastoma tissue compared to non-tumor brain tissue.

FIG. 5 illustrates the difference in the signal level between freshly isolated human tumor tissue and freshly isolated non-tumor human brain tissue assayed ex vivo. Graph 500 displays data points for signal levels prior to treatment continuing through 35 minutes post-treatment. These data points indicate probe activation is approximately 10-times higher in tumor tissue than normal tissue.

Figure 6:
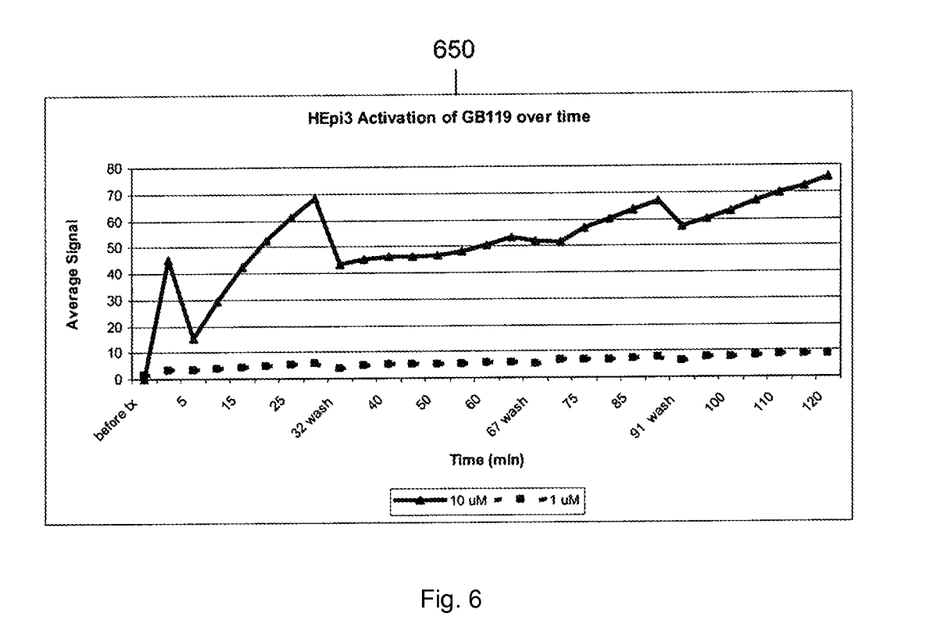
FIG. 6 illustrates imaged abnormal cells and/or cellular products of an abnormal cell associated with epileptic brain tissue after ex vivo topical application of a NIRF probe specific for Cathepsin L.

FIG. 6 illustrates activation of a protease-specific NIRF probe following topical application to freshly resected human epileptic brain tissue. The protease-specific NIRF probe was topically applied to the epileptic tissue ex vivo at a concentration of 10 µM. The graph 650 shows the average signal of each concentration of the protease-specific NIRF probe prior to and following topical application of the protease-specific NIRF probe. The data presented in FIG. 6 illustrates a high level of probe activation following topical application of the protease-specific NIRF probe to epileptic tissue ex vivo in freshly isolated human brain tissue.

Figure 7:
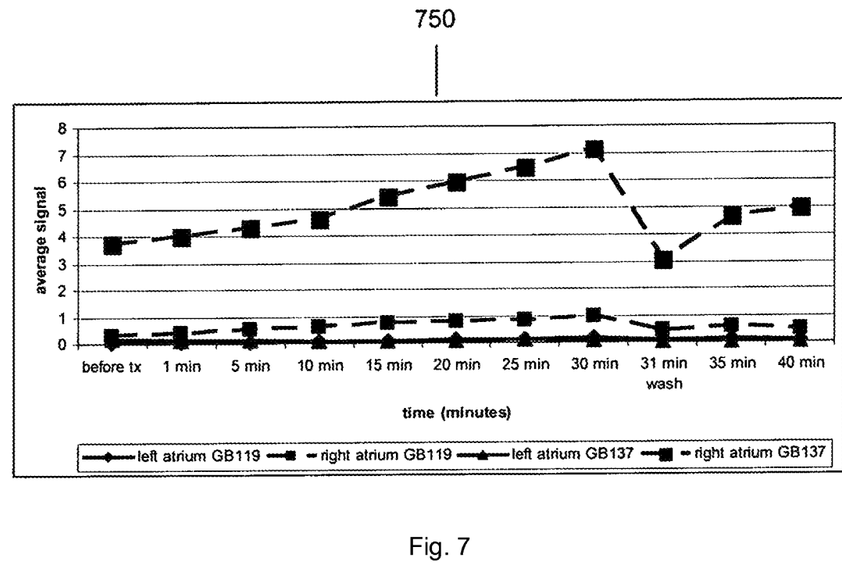
FIG. 7 illustrates imaged abnormal cells and/or cellular products of an abnormal cell in dog heart tissue after topical application of a NIRF probe specific for either Cathepsin L (GB119) or a NIRF probe specific for Cathepsin B and L (GB137).

FIG. 7 illustrates activation of probes following topical application to freshly isolated atrial tissue from a dog heart model designed to mimic human atrial fibrillation. GB119 is a probe that is activated by Cathepsin L. GB137 is a probe that is activated by Cathepsin B and Cathepsin L. The activation levels were translated into average signal and displayed in graphical form in graph 750. The graph shows the average signal of each probe prior to topical probe application to heart tissue and at various time points following topical probe application to heart tissue. The data presented in figure seven illustrates a high level of probe activation following topical application of the probe to heart tissue that has undergone fibrillation in the animal.

Malignant gliomas as a class are highly vascularized and highly invasive tumors that molecularly overexpress MMPs and cysteine proteases that are associated with malignant progression (e.g., Cathepsin L, Cathepsin B). These proteases have been demonstrated to be sufficient for in vivo imaging using NIRF probes administered intravenously. Thus, some example systems and methods may include topical application of protease-specific NIRF imaging probes to facilitate delineating tumor margins during resection. In one example, the protease-specific NIRF imaging probes may be low dose, rapid activating probes that facilitate differentiating normal brain tissue and tumor tissue during surgery. In one example, the NIRF imaging probe may be a Cathepsin specific, optically silent NIRF probe that is activated by Cathepsin B or L. In one example, the NIRF scanner may be an IVIS 200 (Xenogen Inc.) scanner. While Cathepsin specific probes and an IVIS 200 are described, it is to be appreciated that other protease-specific probes and other scanners may be employed. For example, a scanner or NIRF detecting apparatus may be miniaturized and associated with apparatus including a scalpel, a micro-machine, and so on. One example may concern non-cysteine proteases that are over expressed by gliomas and/or other cancers. These non-cysteine proteases may or may not be secreted by the cells. In one example, probes may depend on enzymatic activation to emit a signal. In another example, probes may irreversibly bind to proteases and visually "tag" expressing cells, thereby identifying them as diseased tissue. In yet another example probes may not require activation, but may accumulate at the target due to enzymatic activity. While NIRF imaging probes are described, it is to be appreciated that probes detectable in the range of 400-900 nm may be employed.

Example methods may be better appreciated with reference to flow diagrams. While for purposes of simplicity of explanation, the illustrated methods are shown and described as a series of blocks, it is to be appreciated that the methods are not limited by the order of the blocks, as in different embodiments some blocks may occur in different orders and/or concurrently with other blocks from that shown and described. Moreover, less than all the illustrated blocks may be required to implement an example method. While the figures illustrate various actions occurring in serial, it is to be appreciated that in some examples various actions could occur concurrently, substantially in parallel, and/or at substantially different points in time.

Figure 8:
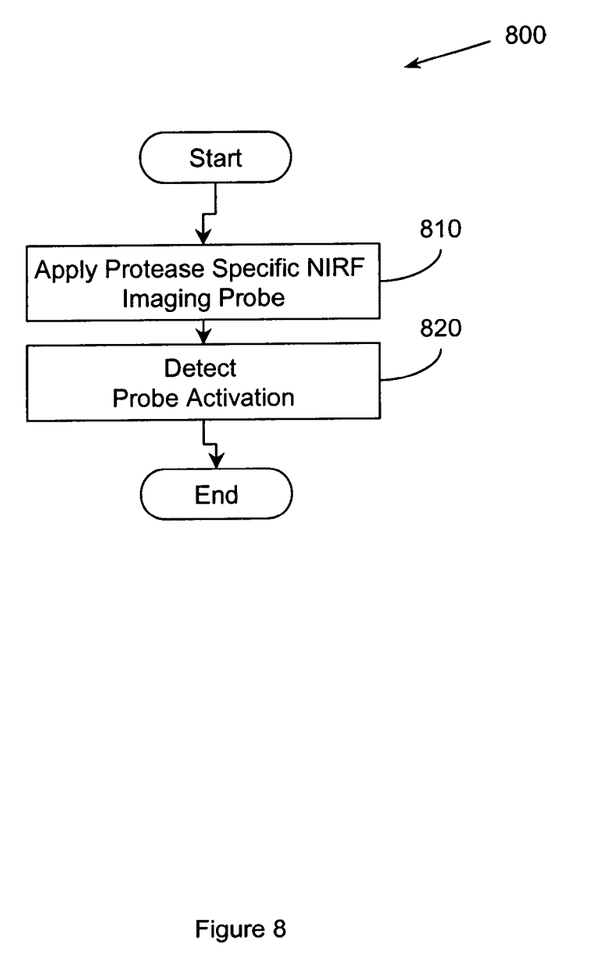
FIG. 8 illustrates an example method associated with identifying abnormal cells.

FIG. 8 illustrates a method 800 associated with identifying abnormal cells. In one example, the abnormal cells may be malignant cells that have infiltrated and/or are beginning to infiltrate at a tumor brain margin. While the brain tumor margin is described, it is to be appreciated that method 800 may be employed more generally to identify abnormal cells that are associated with disease progression. For example, method 800 may be used to visualize foci generating inappropriate electrical activity in the heart and brain thus to facilitate more precise removal of these foci. Method 800 may also be used to visualize abnormal cells and or diseased tissue. Method 800 may be performed in real time during brain or other surgery. Method 800 may include, at 810, topical application of an abnormal cell-marker (e.g., protease specific) optical (e.g., NIRF) imaging probe and, at 820, detecting probe activation using an imaging device (e.g., handheld NIRF scanner). In one example, image data may be gathered. In one example, this image data may be used to determine, at least in part, a radiological treatment. In another example, this image data may be used to control, at least in part, an automated surgical device (e.g., laser, scalpel, micromachine) or to aid in manual guidance of surgery. In one example, the image data can be used to control an intra cardiac ablation procedure. In yet another example, the image data may be used to plan and/or control the delivery of a targeted therapeutic. The targeted therapeutic may be delivered, for example, by a micro-electronic machine or micromachine. It is to be appreciated that method 800 may employ various protease specific NIRF imaging probes and various IOI devices.

Figure 9:
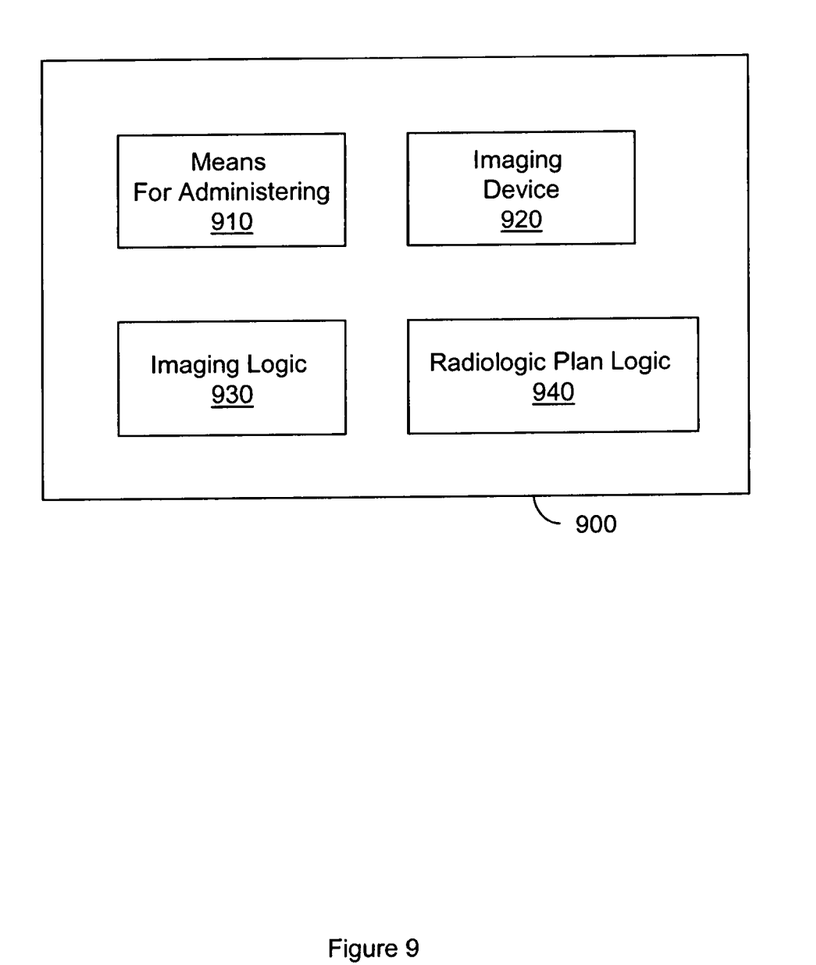
FIG. 9 illustrates an example system associated with identifying abnormal cells.

FIG. 9 illustrates a system 900 associated with identifying abnormal cells. Abnormal cells may include, for example, malignant cells that have infiltrated and/or are beginning to infiltrate at a normal tissue (e.g. brain) tumor margin. Another example of abnormal cells may include cells that display inappropriate electrical activity in the heart and brain. System 900 may include, for example, means 910 for topically administering a probe (e.g., protease specific near infrared (NIRF) imaging probe) to a diseased tissue (e.g., malignant glioma, metastatic brain malignancy, primary tumor of different origin, epileptic tissue, heart tissue displaying inappropriate electrical activity, Barrets Esophagus tissue, displastic tissue). System 900 may also include, for example, an imaging device 920 to detect an interaction (e.g., activation) of the imaging probe with the diseased tissue. The imaging device 920 may be, for example, a handheld NIRF scanner, a scalpel mounted NIRF apparatus, a micro-machine mounted NIRF apparatus, a camera, and so on. In one example, system 900 may also include an imaging logic 930 to detect a tumor margin, to detect a glioma cell infiltrating a tumor brain boundary, and so on. In another example, system 900 may include an imaging logic 930 to detect cells that display inappropriate electrical activity in the heart and brain, and so on. In one example, system 900 may also include a radiologic plan logic 940 that facilitates planning a radiologic treatment based, at least in part, on the detection of a tumor margin and/or on the detection of an infiltrating cell. It is to be appreciated that system 900 may employ various protease-specific NIRF imaging probes and various IOI devices. In one example, imaging device 920 may be a camera that is connected to an ablative laser scalpel. An image acquired by imaging device 920 may be used to control the ablative laser scalpel to destroy remaining diseased tissue.

Figure 10:
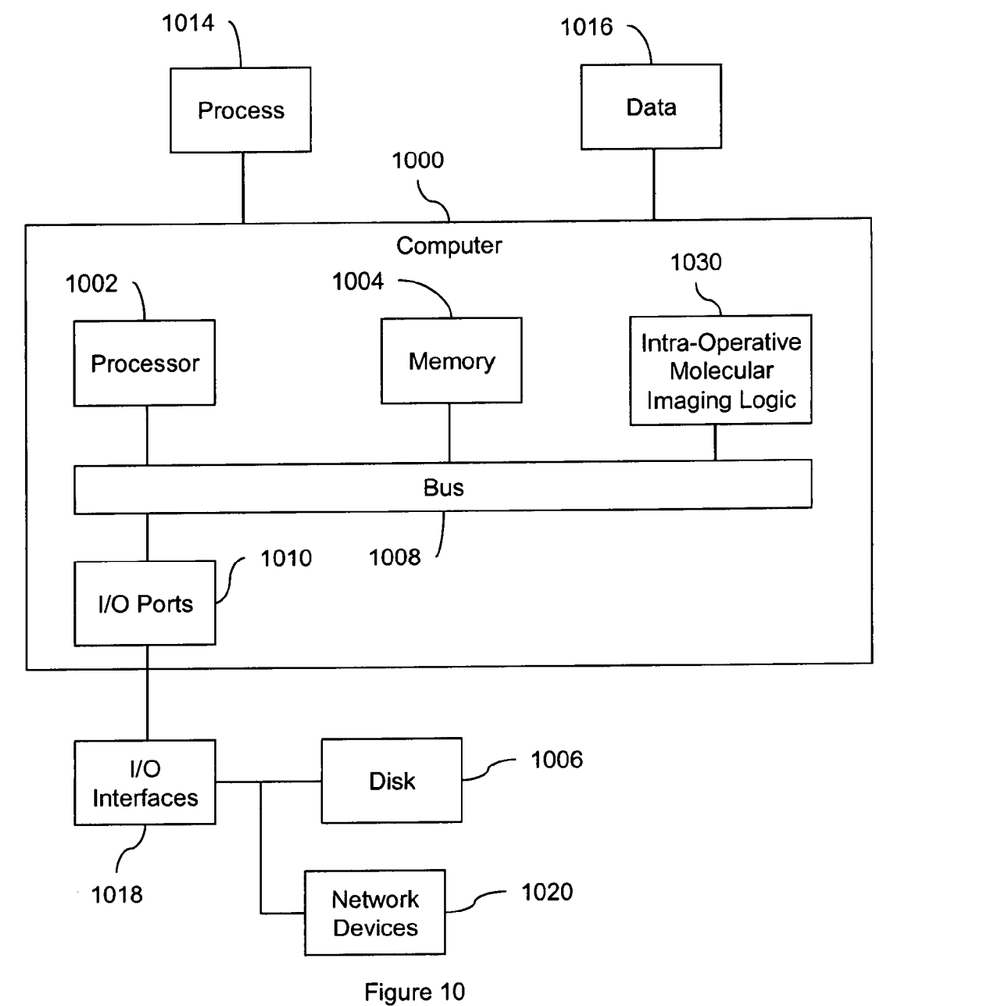
FIG. 10 illustrates an example computing environment in which example systems and methods illustrated herein may operate.

FIG. 10 illustrates an example computing device with which example systems and methods described herein, and equivalents, may operate. The example computing device may be a computer 1000 that includes a processor 1002, a memory 1004, and input/output ports 1010 operably connected by a bus 1008. In one example, the computer 1000 may include an intra-operative molecular imaging logic 1030 to facilitate detecting abnormal cells. In different examples, the logic 1030 may be implemented in hardware, software, firmware, and/or combinations thereof. Thus, the logic 1030 may provide means (e.g., hardware, software, firmware) for receiving image data and means for performing actions including, but not limited to, determining a radiologic therapy, controlling a surgical device, and so on. While the logic 1030 is illustrated as a hardware component attached to the bus 1008, it is to be appreciated that in one example, the logic 1030 could be implemented in the processor 1002.

Generally describing an example configuration of the computer 1000, the processor 1002 may be a variety of various processors including dual microprocessor and other multiprocessor architectures. A memory 1004 may include volatile memory and/or non-volatile memory.

A disk 1006 may be operably connected to the computer 1000 via, for example, an input/output interface (e.g., card, device) 1018 and an input/output port 1010. The disk 1006 may be, for example, a magnetic disk drive, a solid state disk drive, a floppy disk drive, a tape drive, a Zip drive, a flash memory card, and/or a memory stick. Furthermore, the disk 1006 may be a CD-ROM, a CD recordable drive (CD-R drive), a CD rewriteable drive (CD-RW drive), and/or a digital video ROM drive (DVD ROM). The memory 1004 can store a process 1014 and/or a data 1016, for example. The disk 1006 and/or the memory 1004 can store an operating system that controls and allocates resources of the computer 1000.

The bus 1008 may be a single internal bus interconnect architecture and/or other bus or mesh architectures. While a single bus is illustrated, it is to be appreciated that the computer 1000 may communicate with various devices, logics, and peripherals using other busses (e.g., PCIE, SATA, Infiniband, 1394, USB, Ethernet). The bus 1008 can be types including, for example, a memory bus, a memory controller, a peripheral bus, an external bus, a crossbar switch, and/or a local bus.

The computer 1000 may interact with input/output devices via the i/o interfaces 1018 and the input/output ports 1010. Input/output devices may be, for example, a keyboard, a microphone, a pointing and selection device, cameras, video cards, displays, the disk 1006, the network devices 1020, and so on. The input/output ports 1010 may include, for example, serial ports, parallel ports, and USB ports.

The computer 1000 can operate in a network environment and thus may be connected to the network devices 1020 via the i/o interfaces 1018, and/or the i/o ports 1010. Through the network devices 1020, the computer 1000 may interact with a network. Through the network, the computer 1000 may be logically connected to remote computers. Networks with which the computer 1000 may interact include, but are not limited to, a local area network (LAN), a wide area network (WAN), and other networks.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. A method, comprising:
    topically applying a protease-specific, fluorescence imaging probe to tissue in which a targeted cell may be located, the probe being selected from the group consisting of GB119 and GB137 and being activatable by protease-specific activation to produce a visually differentiated signal upon topical application to the cell, the cell comprising an abnormal cell or a diseased cell that secretes a protease that activates the protease-specific, fluorescence imaging probe; and
    detecting, with an imaging device, imaging probe activation induced by an interaction between the imaging probe and the enzyme secreted by the cell, to determine the location of the targeted cell in the tissue.

2. The method of claim 1, the protease being one of, Cathepsin B, and Cathepsin L.

3. The method of claim 1, the cell being a tumor cell.

4. The method of claim 1, the topical application being conducted in a liquid.

5. The method of claim 3, the tumor cell being one of, a metastatic tumor cell, a primary tumor cell, and a metastatic brain malignancy cell.

6. The method of claim 1, including:
    acquiring an image data associated with the probe activation.

7. The method of claim 6, including determining a radiological or surgical treatment based, at least in part, on the image data.

8. The method of claim 6, including controlling a computer-controllable surgical device based, at least in part, on the image data.

9. The method of claim 8, the surgical device being one of, a laser, a scalpel, a gamma knife, and a micro-electronic machine.

10. A method for performing a medical procedure, comprising:
    topically applying a protease-specific, fluorescence imaging probe to tissue in which a targeted cell may be located, the imaging probe being selected from the group consisting of GB119 and GB137 and being activatable by protease-specific activation to produce a visually differentiated signal upon topical application to the cell, the cell comprising an abnormal cell or a diseased cell that secretes a protease that activates the protease-specific, fluorescence imaging probe;
    imaging the tissue to which the probe is topically applied to determine the location of the targeted cell; and
    performing surgery on the imaged targeted cell, where the surgery includes resection and ablation.

11. The method of claim 10, the protease being one of, Cathepsin B, and Cathepsin L.

12. The method of claim 10, where topically applying includes spraying the imaging probe onto a diseased tissue containing the cell.

13. The method of claim 10, where topically applying includes spraying or injecting an imaging probe into a liquid surrounding the cell.

14. The method of claim 10, the cell being located in an animal.

15. The method of claim 10, the cell being located in a human.

16. The method of claim 10, the cell being a tumor cell.

* * * * *